(12) United States Patent
Begtrup et al.

(10) Patent No.: US 10,736,565 B2
(45) Date of Patent: Aug. 11, 2020

(54) SWEAT ELECTROLYTE LOSS MONITORING DEVICES

(71) Applicant: Eccrine Systems, Inc., Cincinnati, OH (US)

(72) Inventors: Gavi Begtrup, Cincinnati, OH (US); Austin Morgan, Bellevue, KY (US); Mikel Larson, Cincinnati, OH (US); Jacob A. Bertrand, Norwood, OH (US); Nicholas Bailey, Cincinnati, OH (US); Cory Newland, Cincinnati, OH (US); Robert Beech, Cincinnati, OH (US); Brian Hanley, Cincinnati, OH (US)

(73) Assignee: Eccrine Systems, Inc., Cincinnati, OH (US)

( * ) Notice: Subject to any disclaimer, the term of this patent is extended or adjusted under 35 U.S.C. 154(b) by 142 days.

(21) Appl. No.: 15/754,141

(22) PCT Filed: Oct. 16, 2017

(86) PCT No.: PCT/US2017/056750
§ 371 (c)(1),
(2) Date: Feb. 21, 2018

(87) PCT Pub. No.: WO2018/071895
PCT Pub. Date: Apr. 19, 2018

(65) Prior Publication Data
US 2019/0008448 A1 Jan. 10, 2019

Related U.S. Application Data

(60) Provisional application No. 62/408,097, filed on Oct. 14, 2016, provisional application No. 62/461,562, (Continued)

(51) Int. Cl.
*A61B 5/00* (2006.01)
*A61B 5/145* (2006.01)
(Continued)

(52) U.S. Cl.
CPC .......... *A61B 5/486* (2013.01); *A61B 5/02055* (2013.01); *A61B 5/1477* (2013.01);
(Continued)

(58) Field of Classification Search
USPC ................................. 600/300–301
See application file for complete search history.

(56) References Cited

U.S. PATENT DOCUMENTS 4,053,381 A 10/1977 Hamblen et al.
4,190,060 A 2/1980 Greenleaf et al.
(Continued)

FOREIGN PATENT DOCUMENTS

EP 0282349 A2 9/1988
EP 0453283 A1 10/1991
(Continued)

OTHER PUBLICATIONS

European Patent Office, Extended European Search Report issued in corresponding European Application No. 18157932.7-1020 dated Jun. 22, 2018, 8 pages.
(Continued)

*Primary Examiner* — Nicole F Lavert

(57) ABSTRACT

Embodiments of the disclosed invention provide devices and methods to incorporate suspension-based, i.e., hydrogel-based and thixotropic compound-based, ion-selective electrodes and reference electrodes into a wearable sweat sensing device. Embodiments of this device are configured to monitor sweat electrolyte concentrations, trends, and ratios under demanding use conditions. The accompanying method includes use of the disclosed device to track fluid
(Continued)

and electrolyte gain and loss in order to produce an electrolyte estimate, such as a sweat electrolyte concentration, a sweat electrolyte concentration trend, a sweat rate, or a concentration ratio between a plurality of electrolytes.

15 Claims, 8 Drawing Sheets

Related U.S. Application Data filed on Feb. 21, 2017, provisional application No. 62/526,810, filed on Jun. 29, 2017.

(51) Int. Cl.

| | | |
|---|---|---|
| *A61B 5/1477* | (2006.01) | |
| *A61B 5/0205* | (2006.01) | |
| *A61B 5/20* | (2006.01) | |
| *G01N 33/487* | (2006.01) | |
| *A61B 5/11* | (2006.01) | |
| *A61B 5/024* | (2006.01) | |
| *A61B 5/053* | (2006.01) | |
| *A61B 5/01* | (2006.01) | |

(52) U.S. Cl.
CPC ...... *A61B 5/14517* (2013.01); *A61B 5/14546* (2013.01); *A61B 5/201* (2013.01); *A61B 5/4266* (2013.01); *A61B 5/4872* (2013.01); *A61B 5/4875* (2013.01); *A61B 5/6801* (2013.01); *A61B 5/6833* (2013.01); *A61B 5/7405* (2013.01); *A61B 5/7435* (2013.01); *A61B 5/7455* (2013.01); *A61B 5/7475* (2013.01); *G01N 33/48707* (2013.01); *G01N 33/48792* (2013.01); *A61B 5/01* (2013.01); *A61B 5/02438* (2013.01); *A61B 5/0533* (2013.01); *A61B 5/0537* (2013.01); *A61B 5/1118* (2013.01); *A61B 2560/0242* (2013.01)

(56) References Cited

U.S. PATENT DOCUMENTS

| | | | |
|---|---|---|---|
| 4,542,751 | A | 9/1985 | Webster et al. |
| 4,756,314 | A | 7/1988 | Eckenhoff et al. |
| 4,820,263 | A | 4/1989 | Spevak et al. |
| 5,036,861 | A | 8/1991 | Sembrowich et al. |
| 5,050,604 | A | 9/1991 | Reshef et al. |
| 5,140,985 | A | 8/1992 | Schroeder et al. |
| 5,246,003 | A | 9/1993 | Delonzor |
| 5,437,999 | A | 8/1995 | Diebold et al. |
| 5,438,984 | A | 8/1995 | Schoendorfer |
| 5,556,789 | A | 9/1996 | Goerlach-Graw et al. |
| 5,690,893 | A | 11/1997 | Ozawa et al. |
| 5,814,599 | A | 9/1998 | Mitragotri et al. |
| 5,944,662 | A | 8/1999 | Schoendorfer |
| 6,175,752 | B1 | 1/2001 | Say et al. |
| 6,198,953 | B1 | 3/2001 | Webster et al. |
| 6,256,533 | B1 | 7/2001 | Yuzhakov et al. |
| 6,269,265 | B1 | 7/2001 | Anderson |
| 6,299,578 | B1 | 10/2001 | Kurnik et al. |
| 6,592,529 | B2 | 7/2003 | Marett |
| 6,666,821 | B2 | 12/2003 | Keimel |
| 7,044,911 | B2 | 5/2006 | Drinan et al. |
| 7,190,986 | B1 | 3/2007 | Hannula et al. |
| 7,219,534 | B2 | 5/2007 | Campbell |
| 7,378,054 | B2 | 5/2008 | Karmali |
| 7,383,072 | B2 | 6/2008 | Edmonson et al. |
| 7,384,396 | B2 | 6/2008 | Samuels et al. |
| 7,749,445 | B2 | 7/2010 | Masters |
| 7,800,494 | B2 | 9/2010 | Kim |
| 7,813,780 | B2 | 10/2010 | Shah et al. |
| 7,842,234 | B2 | 11/2010 | Lauks et al. |
| 7,959,791 | B2 | 6/2011 | Kjaer et al. |
| 8,125,539 | B2 | 2/2012 | Takashima |
| 8,128,889 | B2 | 3/2012 | Fujimoto et al. |
| 8,252,248 | B2 | 8/2012 | Kramer |
| 8,391,946 | B2 | 3/2013 | Sugenoya et al. |
| 8,565,850 | B2 | 10/2013 | Martinsen et al. |
| 8,593,287 | B2 | 11/2013 | Hayter et al. |
| 8,617,067 | B2 | 12/2013 | Jain et al. |
| 9,133,024 | B2 | 9/2015 | Phan et al. |
| 9,867,539 | B2 | 1/2018 | Heikenfeld et al. |
| 2002/0091312 | A1 | 7/2002 | Berner et al. |
| 2003/0135100 | A1 | 7/2003 | Kim et al. |
| 2003/0201194 | A1 | 10/2003 | Heller et al. |
| 2004/0215098 | A1 | 10/2004 | Barton et al. |
| 2004/0249310 | A1 | 12/2004 | Shartle et al. |
| 2004/0260154 | A1 | 12/2004 | Sidelnik et al. |
| 2004/0267189 | A1 | 12/2004 | Mavor et al. |
| 2005/0069925 | A1 | 3/2005 | Ford et al. |
| 2005/0106713 | A1 | 5/2005 | Phan et al. |
| 2005/0177035 | A1 | 8/2005 | Botvinick et al. |
| 2005/0192528 | A1 | 9/2005 | Tapper |
| 2005/0197554 | A1 | 9/2005 | Polcha |
| 2005/0228297 | A1 | 10/2005 | Banet et al. |
| 2005/0280531 | A1 | 12/2005 | Fadem et al. |
| 2006/0009697 | A1 | 1/2006 | Banet et al. |
| 2006/0062852 | A1 | 3/2006 | Holmes |
| 2006/0127964 | A1 | 6/2006 | Ford et al. |
| 2006/0253011 | A1 | 11/2006 | Edmonson et al. |
| 2006/0254341 | A1 | 11/2006 | Campbell |
| 2007/0027383 | A1 | 2/2007 | Peyser et al. |
| 2007/0032731 | A1 | 2/2007 | Lovejoy et al. |
| 2007/0179371 | A1 | 8/2007 | Peyser et al. |
| 2008/0015494 | A1 | 1/2008 | Santini, Jr. et al. |
| 2008/0045816 | A1 | 2/2008 | Jang et al. |
| 2008/0154179 | A1 | 6/2008 | Cantor et al. |
| 2008/0286349 | A1 | 11/2008 | Nomoto et al. |
| 2008/0302659 | A1 | 12/2008 | Sheppard, Jr. et al. |
| 2008/0306362 | A1 | 12/2008 | Davis |
| 2009/0076345 | A1 | 3/2009 | Manicka et al. |
| 2009/0159442 | A1 | 6/2009 | Collier et al. |
| 2009/0204008 | A1 | 8/2009 | Beilin |
| 2009/0270704 | A1 | 10/2009 | Peyser et al. |
| 2010/0044224 | A1 | 2/2010 | Kataky |
| 2010/0063372 | A1 | 3/2010 | Potts |
| 2010/0130843 | A1 | 5/2010 | Caceres Galvez et al. |
| 2010/0132485 | A1 | 6/2010 | Erez et al. |
| 2010/0198521 | A1 | 8/2010 | Haick |
| 2011/0004072 | A1 | 1/2011 | Fletcher |
| 2011/0054273 | A1 | 3/2011 | Omoda |
| 2011/0079521 | A1 | 4/2011 | Revol-Cavalier |
| 2011/0118656 | A1 | 5/2011 | Eckhoff et al. |
| 2011/0178380 | A1 | 7/2011 | Chowdhury |
| 2011/0196283 | A1 | 8/2011 | Imran et al. |
| 2011/0208458 | A1 | 8/2011 | Pinter et al. |
| 2011/0275918 | A1 | 11/2011 | Yamashita et al. |
| 2012/0004570 | A1 | 1/2012 | Shimizu et al. |
| 2012/0028283 | A1 | 2/2012 | Hoss et al. |
| 2012/0119906 | A1 | 5/2012 | Kountotsis |
| 2012/0123220 | A1 | 5/2012 | Iyer et al. |
| 2012/0165626 | A1 | 6/2012 | Irina et al. |
| 2012/0191147 | A1 | 7/2012 | Rao et al. |
| 2012/0209226 | A1 | 8/2012 | Simmons et al. |
| 2012/0229661 | A1 | 9/2012 | Sekiguchi et al. |
| 2012/0277697 | A1 | 11/2012 | Haghgooie et al. |
| 2012/0285829 | A1 | 11/2012 | Mount et al. |
| 2012/0317430 | A1 | 12/2012 | Rahman et al. |
| 2013/0006079 | A1 | 1/2013 | Feldman et al. |
| 2013/0010108 | A1 | 1/2013 | Hashizume et al. |
| 2013/0013028 | A1 | 1/2013 | Kriksunov et al. |
| 2013/0053668 | A1 | 2/2013 | Lin |
| 2013/0079605 | A1 | 3/2013 | Bandaru et al. |
| 2013/0099937 | A1 | 4/2013 | Azimi |
| 2013/0108667 | A1 | 5/2013 | Soikum et al. |
| 2013/0123595 | A1 | 5/2013 | Currie et al. |
| 2013/0183399 | A1 | 7/2013 | Blow et al. |
| 2013/0245388 | A1 | 9/2013 | Rafferty et al. |
| 2013/0306491 | A1 | 11/2013 | Briman et al. |
| 2013/0317318 | A1 | 11/2013 | Tartz et al. |
| 2013/0317333 | A1 | 11/2013 | Yang et al. |
| 2014/0012114 | A1 | 1/2014 | Zevenbergen et al. |

(56) References Cited

U.S. PATENT DOCUMENTS

| | | |
|---|---|---|
| 2014/0025000 A1 | 1/2014 | Currie et al. |
| 2014/0206977 A1 | 7/2014 | Bahney et al. |
| 2014/0221792 A1 | 8/2014 | Miller et al. |
| 2014/0273925 A1 | 9/2014 | Burgett et al. |
| 2014/0275862 A1 | 9/2014 | Kennedy |
| 2014/0276220 A1 | 9/2014 | Briscoe et al. |
| 2014/0343371 A1 | 11/2014 | Sowers, II et al. |
| 2015/0057515 A1 | 2/2015 | Hagen et al. |
| 2015/0112164 A1 | 4/2015 | Heikenfeld et al. |
| 2015/0112165 A1 | 4/2015 | Heikenfeld |
| 2015/0289820 A1 | 4/2015 | Miller et al. |
| 2016/0058354 A1 | 3/2016 | Phan et al. |
| 2016/0066828 A1 | 3/2016 | Phan et al. |
| 2016/0157768 A1 | 6/2016 | Braig et al. |
| 2017/0100035 A1 | 4/2017 | Heikenfeld |
| 2017/0100071 A1 | 4/2017 | Heikenfeld |
| 2017/0215773 A1 | 8/2017 | Heikenfeld et al. |

FOREIGN PATENT DOCUMENTS

| | | | |
|---|---|---|---|
| EP | 1575010 A1 | 9/2005 | |
| EP | 1637889 A1 | 3/2006 | |
| EP | 2551784 A1 | 1/2013 | |
| EP | 2783725 A1 | 10/2014 | |
| WO | 1990011519 A1 | 10/1990 | |
| WO | 1994014062 A1 | 6/1994 | |
| WO | 2000014535 A1 | 3/2000 | |
| WO | 2001088525 A1 | 11/2001 | |
| WO | 2006133101 A2 | 12/2006 | |
| WO | 2007097754 A1 | 8/2007 | |
| WO | 2007146047 A1 | 12/2007 | |
| WO | 2008058014 A2 | 5/2008 | |
| WO | 2008083687 A1 | 7/2008 | |
| WO | 2008095940 A1 | 8/2008 | |
| WO | 2009004001 A1 | 1/2009 | |
| WO | 2009052321 A2 | 4/2009 | |
| WO | 2010017578 A1 | 2/2010 | |
| WO | 2010021536 A2 | 2/2010 | |
| WO | 2011008581 A2 | 1/2011 | |
| WO | 2011117952 A1 | 9/2011 | |
| WO | 2013111409 A1 | 8/2013 | |
| WO | 2013181436 A1 | 12/2013 | |
| WO | 2014001577 A1 | 1/2014 | |
| WO | 2014025430 A3 | 5/2014 | |
| WO | 2015058065 A1 | 4/2015 | |
| WO | 2016007944 A2 | 1/2016 | |
| WO | 2016049019 A1 | 3/2016 | |
| WO | 2016090189 A1 | 6/2016 | |
| WO | 2016130905 A1 | 8/2016 | |
| WO | 2016138087 A1 | 9/2016 | |
| WO | WO-2016138087 A1 * | 9/2016 | ........... A61B 5/6843 |
| WO | 2017019602 A1 | 2/2017 | |
| WO | 2017070640 A1 | 4/2017 | |

OTHER PUBLICATIONS

International Searching Authority, Search Report and Written Opinion issued in corresponding International Application No. PCT/US2015/055756 dated Apr. 8, 2016, 17 pages.

International Searching Authority, Search Report and Written Opinion issued in corresponding International Application No. PCT/US2016/019282 dated Jul. 27, 2016, 18 pages.

International Searching Authority, Search Report and Written Opinion issued in corresponding International Application No. PCT/US2016/053625 dated Dec. 8, 2016, 14 pages.

International Searching Authority, Search Report and Written Opinion issued in corresponding International Application No. PCT/US2017/042677 dated Nov. 17, 2017, 13 pages.

International Searching Authority, Search Report and Written Opinion issued in corresponding International Application No. PCT/US2017/056750 dated Dec. 22, 2017, 9 pages.

* cited by examiner

SWEAT ELECTROLYTE LOSS MONITORING DEVICES

CROSS-REFERENCE TO RELATED APPLICATIONS

The present application is a continuation-in-part of PCT/US17/56750, filed Oct. 16, 2017; and claims priority to U.S. Provisional Application No. 62/408,097, filed Oct. 14, 2016; U.S. Provisional Application No. 62/461,562, filed Feb. 21, 2017; and U.S. Provisional Application No. 62/526,810, filed Jun. 29, 2017, and has specification that builds upon PCT/US2016/36038, filed Jun. 6, 2016, the disclosures of which are hereby incorporated herein by reference in their entirety.

BACKGROUND OF THE INVENTION

Non-invasive biosensing technologies have enormous potential for applications ranging from athletics, to neonatology, to pharmacological monitoring, to personal digital health. Among the biofluids potentially used for physiological monitoring (e.g., sweat, blood, urine, saliva, tears), sweat has arguably the least predictable sampling rate in the absence of technological solutions. An excellent summary is provided by Sonner, et al. in the 2015 article titled "The microfluidics of the eccrine sweat gland, including biomarker partitioning, transport, and biosensing implications," *Biomicrofluidics* 9, 031301, included by reference herein in its entirety. However, with proper application of technology, sweat can be made to outperform other non-invasive or less invasive biofluids in predictable sampling. As a result, sweat ducts can provide a route of access to many of the same biomarkers, chemicals, or solutes that are carried in blood and can provide significant information enabling diagnosis of ailments, health status, toxins, performance, and other physiological attributes even in advance of any physical sign.

However, one challenge to creating accurate sweat sensing devices is developing sensors that are practical for use in a wearable, semi-disposable device, when the required sensitivity and specificity of such sensors is typically achieved in expensive bench-top configurations that are afforded stable operating environments. Sweat sensors, however, must work within a device that is sufficiently small and robust to be worn on the body. These devices must operate in a dynamic environment, and be inexpensive enough to be periodically replaced. When bench-top ion selective electrodes ("ISE"), and their accompanying reference electrodes, are moved from the laboratory to a sweat sensor, they must be greatly reduced in size, are often deposited on a flexible substrate, and exposed to skin. However, such configurations are prone to drift due to their small size, may experience interference from the body, may delaminate from the substrate, or be abraded through contact with skin or other device components. The Horiba LaquaTwin, covered by U.S. Pat. No. 5,200,706, successfully incorporates ISEs into a hand-held device for water sampling. However, these sensors are still too large and expensive for use in wearable sweat sensors.

What is needed are simple, yet robust methods to incorporate ISEs and reference electrodes into wearable configurations that are free from drift, delamination, and abrasion over the use period of a sweat sensing device. In particular, sweat sensing devices hold tremendous promise for use in workplace safety, athletic, and military settings. One potential application that can improve personal safety and performance in these settings, is a robust, wearable sweat electrolyte loss monitor. As disclosed herein, a sweat sensing device is configured to monitor sweat electrolyte concentrations, ratios and trends under demanding use conditions.

SUMMARY OF THE INVENTION

Embodiments of the disclosed invention provide devices and methods to incorporate suspension-based, i.e., hydrogel-based and thixotropic compound-based, ion-selective electrodes and reference electrodes into a wearable sweat sensing device. Embodiments of this device are configured to monitor sweat electrolyte concentrations, trends, and ratios under demanding use conditions. The accompanying method includes use of the disclosed device to track fluid and electrolyte gain and loss in order to produce an electrolyte estimate, such as a sweat electrolyte concentration, a sweat electrolyte concentration trend, a sweat rate, or a concentration ratio between a plurality of electrolytes.

BRIEF DESCRIPTION OF THE DRAWINGS

The objects and advantages of the disclosed invention will be further appreciated in light of the following detailed descriptions and drawings in which.

DEFINITIONS

Figure 1:
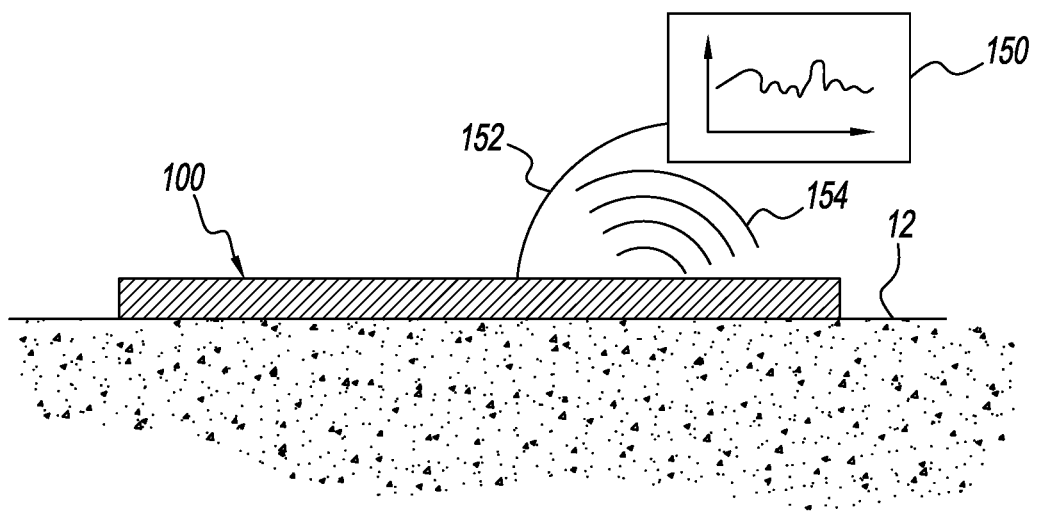
FIG. 1 is an example sweat sensing device of the present disclosure.

A variety of definitions are now provided, these definitions gaining further appreciation and scope in the detailed description and embodiments of the disclosed invention.

As used herein, "sweat" means a biofluid that is primarily sweat, such as eccrine or apocrine sweat, and may also include mixtures of biofluids such as sweat and blood, or sweat and interstitial fluid, so long as advective transport of the biofluid mixtures (e.g., flow) is primarily driven by sweat.

"Sweat sensor" means any type of sensor that measures a state, presence, flow rate, solute concentration, solute presence, in absolute, relative, trending, or other ways in sweat biofluid. Sweat sensors can include, for example, potentiometric, amperometric, impedance, optical, mechanical, antibody, peptide, aptamer, or other means known by those skilled in the art of sensing or biosensing.

"Analyte" means a substance, molecule, ion, or other material that is measured by a sweat sensing device.

"Electrolyte" means solutes within human body fluids and tissues that include all acids and bases, inorganic salts, and some proteins. Examples of interest include $Na^+$, $Cl^-$, $H^+$, $K^+$, $NH_4^+$, $Ca^+$, $HCO_3^-$, and $Mg^+$.

"Measured" can imply an exact or precise quantitative measurement and can include broader meanings such as, for example, measuring a relative amount of change of something. Measured can also imply a binary measurement, such as 'yes' or 'no' type measurements.

"Chronological assurance" means the sampling rate or sampling interval that assures measurement(s) of analytes in biofluid in terms of the rate at which measurements can be made of new biofluid analytes emerging from the body. Chronological assurance may also include a determination of the effect of sensor function, potential contamination with previously generated analytes, other fluids, or other measurement contamination sources for the measurement(s). Chronological assurance may have an offset for time delays in the body (e.g., a well-known 5 to 30 minute lag time between analytes in blood emerging in interstitial fluid), but the resulting sampling interval (defined below) is independent of lag time, and furthermore, this lag time is inside the body, and therefore, for chronological assurance as defined above and interpreted herein, this lag time does not apply.

"Analyte-specific sensor" means a sensor specific to an analyte and performs specific chemical recognition of the analytes presence or concentration (e.g., ion-selective electrodes, enzymatic sensors, electro-chemical aptamer based sensors, etc.). For example, sensors that sense impedance or conductance of a fluid, such as sweat, are excluded from the definition of "analyte-specific sensor" because sensing impedance or conductance merges measurements of all ions in sweat (i.e., the sensor is not chemically selective; it provides an indirect measurement). Sensors could also be optical, mechanical, or use other physical/chemical methods which are specific to a single analyte. Further, multiple sensors can each be specific to one of multiple analytes.

"Sweat flow rate sensing component" is any component or components which measure the sweat rate in at least one portion of a sweat sensing or collecting device.

"Hydrogel" means a substantially dilute polymeric material which is primarily water, and that exhibits little or no flow when in the steady-state due to a three-dimensional cross-linked network of a chemically incorporated additional material.

"Thixotropic compound" means a material that is mechanically stabilized or viscous under static conditions, but that will flow (or become less viscous) when shaken, agitated, sheared or otherwise manipulated.

"Suspension-based electrode" means an ISE or reference electrode that incorporates hydrogel-based or thixotropic compound-based suspension materials.

"Operation and compliance warning" means an alert generated by the sweat sensing device and relayed to the system user if a reading indicates a device is not in adequate skin contact.

DETAILED DESCRIPTION OF THE INVENTION

The present disclosure provides a sweat sensing device configured to monitor electrolyte concentrations, trends and ratios while a device wearer is participating in physical activity in order to improve the wearer's safety or physical performance. Any time an individual sweats, s/he loses electrolytes. Under extreme physical conditions, such as intense heat or prolonged physical exertion, individuals can lose sufficient quantities of electrolytes through sweat, so that numerous essential biological processes become impaired. For example, excessive sodium loss, or hyponatremia, can manifest as headaches, nausea, vomiting, muscle spasms, and seizures. Similarly, excessive loss of $K^+$, or hypokalemia, can manifest as muscle cramps, heart palpitations, or delirium. Other electrolyte imbalance disorders include alkalosis, hypochloremia, hypocalcemia, hypomagnesemia, and loss of bicarbonates ($HCO_3^-$). Monitoring the loss and replenishment of electrolytes can therefore improve the safety and performance of individuals operating under extreme electrolyte loss conditions.

The disclosed invention will be primarily, but not entirely, limited to devices, methods and sub-methods using wearable sweat sensing devices. Therefore, although not described in detail here, other essential steps which are readily interpreted from or incorporated along with the present invention shall be included as part of the disclosed invention. The disclosure provides specific examples to portray inventive steps, but which will not necessarily cover all possible embodiments commonly known to those skilled in the art. For example, the specific invention will not necessarily include all obvious features needed for operation. Several specific, but non-limiting, examples can be provided as follows. The invention includes reference to the article in press for publication in the journal *IEEE Transactions on Biomedical Engineering*, titled "Adhesive RFID Sensor Patch for Monitoring of Sweat Electrolytes"; the article published in the journal *AIP Biomicrofluidics*, 9 031301 (2015), titled "The Microfluidics of the Eccrine Sweat Gland, Including Biomarker Partitioning, Transport, and Biosensing Implications"; as well as PCT/US15/55756, and PCT/US16/19282; all four of which are included herein by reference in their entirety.

The present disclosure applies at least to any type of sweat sensing device that measures sweat, sweat generation rate, sweat chronological assurance, its solutes, solutes that transfer into sweat from skin, a property of or things on the surface of skin, or properties or things beneath the skin. The disclosure applies to sweat sensing devices which can take on forms including patches, bands, straps, portions of clothing or equipment, or any suitable mechanism that reliably brings sweat collecting, and/or sweat sensing technology into intimate proximity with sweat as it is generated.

Certain embodiments of the invention show sensors as simple individual elements. It is understood that many sensors require two or more electrodes, reference electrodes, or additional supporting technology or features that are not captured in the description herein. Sensors are preferably electrochemical in nature, but may also include electrical, optical, chemical, mechanical, or other known biosensing mechanisms. Sensors can be in duplicate, triplicate, or more, to provide improved data and readings. Sensors may be referenced herein by what the sensor is sensing, for example: an analyte specific sensor; an impedance sensor; a sweat volume sensor; a sweat rate sensor; or a solute generation rate sensor. Certain embodiments of the disclosed invention show sub-components of what would be sweat sensing devices with more sub-components needed for use of the device in various applications, which are obvious (such as a battery), and for purpose of brevity and focus on inventive aspects, are not explicitly shown in the diagrams or described in the embodiments of the present disclosure.

Sweat is known to contain a large number of compounds that could be used to indicate an individual's physiological state. In general, determining an individual's physiological state is a significant challenge. Not only is every individual different in terms of how a physiological state may present, but even a simple physiological state or disorder is a complex set of biological processes that does not readily lend itself to reduction. Consequently, a definitive diagnosis of a physiological condition often is not possible. Among the most common substances found in sweat are the following: $Na^+$, $Cl^-$, $K^+$, Ammonium ($NH_4^+$), urea, lactate, glucose, serine, glycerol, cortisol, and pyruvate. In addition to these common sweat analytes, each physiological condition may also have particular sweat analytes that will prove informative for indicating that physiological state. For example, blood creatinine levels have proven useful for indicating hydration levels, which also may prove true for sweat.

To date, there have been few studies linking sweat analytes or analyte concentrations to physiological states. Among these are studies linking increased sweat chloride levels with cystic fibrosis, or a spike in chloride levels with ovulation. It will likely be necessary to build data across multiple individuals correlating physiological states with sweat sensor readings. By this means, a given physiological state will manifest and a discernible sweat analyte signature will be detectible by a sweat sensing device.

Further, translation of analyte concentrations and ratios to meaningful physiological information will have to account for a number of variabilities unrelated to differences in concentrations. For example, sweat concentrations of analytes relative to blood or plasma concentrations are known to vary depending on sweat rate, the body location from which a sample is taken, kidney or liver disease or function, external temperatures, and other factors. To develop meaningful physiological information, it will therefore be necessary to develop algorithms and techniques that reflect how the various analyte signatures change in response to these variabilities.

Sweat contains a number of electrolytes in varying concentrations, including the following: $Na^+$ (10-100 mM), $Cl^-$ (10-100 mM), $H^+$ (0.1 mM-0.0001 mM), $K^+$ (1-24 mM), $NH_4^+$ (0.5-8 mM), $Ca^+$ (~0.5 mM), and $Mg^+$. Sweat also includes a variety of other electrolytes in lower concentrations.

Specific to determining an individual's electrolyte status, a sweat sensing device can be configured to accurately measure electrolyte loss amounts, trends and ratios. Electrolyte loss is a key component of a larger picture that constitutes an individual's overall electrolyte status, which includes at least the following three basic factors: 1) electrolyte inputs through an individual's diet; 2) electrolyte redistribution within the individual's body; and 3) electrolyte loss.

At a basic level, electrolyte inputs are those electrolytes consumed through food or fluids, and which are absorbed from the digestive tract for use throughout the body. Absorption is a complicated process that may be affected by the amount of food or fluids consumed, the existing levels or ratios of electrolytes in the body, the activity taking place during absorption, circulation levels to the digestive tract, the kinetics of absorption of the different electrolytes, and other factors.

Electrolyte redistribution is a continual process by which the body manages electrolyte concentrations in extracellular fluid by moving electrolytes among various repositories in the body. These repositories include intracellular fluid, extracellular fluid, interstitial fluid, plasma volume, and certain tissues, such as skeletal repositories of calcium. Electrolytes move among the different repositories based on osmotic and hydrostatic pressure gradients, may be controlled by selectively permeable membranes, or may respond to homeostatic control mechanisms triggered by extracellular fluid concentrations of particular electrolytes.

Electrolyte loss may be through urine excretion, sweat excretion, or gastrointestinal tract excretion. Electrolyte loss amounts are influenced by homeostasis feedback loops, which control electrolyte retention and excretion processes, as well as water retention and excretion processes. Additionally, electrolyte loss is complicated by individual factors, such as the health of key organs, e.g., the kidneys, or the relative dysfunction in the body's homeostasis mechanisms. A non-exhaustive list of potential considerations that may inform sweat electrolyte loss include the following: sweat rate, hydration status, electrolyte intake during monitoring period, exercise intensity, body temperature, environmental conditions, heat acclimation, fitness level, routine daily electrolyte intake, BMI, body location of device, phenotype, sex, age, medical conditions, and pharmaceutical use.

The disclosed invention provides accurate measurements of sweat electrolyte loss, which is a key element for determining a device wearer's electrolyte condition. Generally, sweat electrolyte loss and sweat rate are highly correlated, therefore, the disclosed device can be configured with sweat rate sensors, e.g., volumetric sweat rate sensors, ISEs, or micro-thermal flow rate sensors, as well as algorithms capable of determining sweat rate, as disclosed in PCT/US2016/36038 and U.S. Ser. No. 15/653,494, which are hereby incorporated by reference herein in their entirety.

Various studies in eccrinology have characterized the variance in molarity of $Na^+$, $Cl^-$ and $K^+$ with sweat rate. See Sato, K., et al., "Biology of sweat glands and their disorders," *J. of the Am. Academy of Dermatology*, p. 552, 20/4/April 1989. $Na^+$ and $Cl^-$ enter sweat in the secretory coil of the eccrine sweat gland, and at negligible sweat rates, are isotonic with interstitial fluid concentrations of $Na^+$ and $Cl^-$. Bovell, *Journal of Local and Global Health Science*, p. 9, 2015:5. With the initiation of sweating, $Cl^-$ is pumped into the lumen of the gland, where its negative electrical potential pulls in $Na^+$. The $Na^+$ and $Cl^-$ combine to form NaCl, which creates an osmotic gradient that draws water into the lumen. As the newly created sweat moves out of the secretory coil, $Na^+$, with $Cl^-$ in tow, is reabsorbed through the duct and re-enters the interstitial fluid.

At lower sweat rates, 0.0 to 0.4 $\mu L/cm^2/min$, relatively more of the $Na^+$ and are reabsorbed by the duct so that sweat reaching the skin has lower concentrations of $Na^+$ and $Cl^-$. Amano, T., et al., "Determination of the maximum rate of eccrine sweat glands' ion readsorption using galvanic skin conductance to local sweat rate relationship," *Eur. J. Appl. Physiology*, p. 4, DOI 10.1007/s00421-015-3275-9. Initially, between 0.2 and 0.4 $\mu L/cm^2/min$ sweat rate, the $Na^+$ gland reabsorption rate is at is maximum (around 85%), which translates to $Na^+$ concentration of 10-15 mM. Sato, K., et al., "Biology of sweat glands and their disorders," *J. of the Am. Academy of Dermatology*, p. 552, 20/4/April 1989, p. 552; Buono, M., et al., "$Na^+$ secretion rate increases proportionally more than the $Na^+$ reabsorption rate with increases in sweat rate," *J. Appl. Physiology*, 105:1044-1048, 2008. As sweat rate increases, the amount and speed of $Na^+$ flowing through the duct overwhelms the reabsorption mechanism, so that at sweat rates above 0.4 $\mu L/cm^2/min$, the duct absorbs a significantly lower percentage of $Na^+$, down to about 65% of $Na^+$ at a sweat rate of 0.8 $\mu L/cm^2/min$. Buono, M., et al. As a result, $Na^+$ concentrations show a linear increase with increases in sweat rate in the range of about 20 mEq/L for a 0.4 µL/cm$^2$/min sweat rate, to 60 mEq/L for a 1.5 µL/cm$^2$/min sweat rate. Allen, J., et al., "Influence of acclimatization on sweat sodium concentration," *J. of Applied Physiology*, 30/5/May 1971, at 710; Bovell, at 11; see also, Buono, p. 1025. (0.25 µL/cm$^2$/min sweat rate correlated to 20 mM/L Na$^+$, 0.9 µL/cm$^2$/min sweat rate correlated to 55 mM/L concentrations roughly correspond to Na$^+$ levels for various sweat rates, but are usually 20 mM less. Sato, K., et al. For individuals that acclimatize to warmer environments, or who engage in physical conditioning, the body's ability to reabsorb Na$^+$ improves, and sweat profiles for these individuals will tend to have sweat Na$^+$ concentrations about 15 mM lower than for unconditioned individuals. Allen, J., et al., at 710.

Similar examination of K$^+$ molarity as it changes with sweat rate reveals an analyte that can function as a reference for a number of sweat applications, including the determination of sweat rate. Unlike Na$^+$ and the rate of K$^+$ excretion by the sweat gland does not accelerate with sweat rate increase, and K$^+$ is not reabsorbed by the duct in significant amounts. As a result, K$^+$ concentration remains relatively steady throughout the range of sweat rates. At negligible sweat rates, K$^+$ concentration in the secretory coil corresponds to plasma concentrations of about 3-4 mM. Baker, L., et al., "Comparison of regional patch collection vs. whole body washdown for measuring sweat sodium and potassium loss during exercise," *J. Appl. Physiology*, 107: 887-895, 2009. At very low sweat rates, K$^+$ tends to enter sweat at increased levels, i.e., up to 9 mM, before settling to a concentration of about 6 mM. Sato, K., et al.; Bovell, at 11. It is expected that the loss amounts trends and ratios for other electrolytes of interest will also display dependence on sweat rate, which may be characterized and detected by sweat sensing devices of the disclosed invention.

With reference to FIG. 1, a representative sweat sensing device 1 to which the present disclosure applies is placed on or near skin 12. The sweat sensing device may be fluidically connected to skin or regions near skin through microfluidics or other suitable techniques. The device 1 is in wired communication 110 or wireless communication 120 with a reader device 130, which could be a smart phone or, tablet computer, or other portable electronic device, or for some devices, the device 1 and reader device 130 can be combined. The reader device may also be in communication with computer network that can provide access to database information capable of informing device function. In a preferred embodiment, communication 152 or 120 is not constant and could be a simple one-time data upload to the device at the initiation of use, and periodic data downloads from the device once the device has completed its measurements of sweat.

As disclosed, a sweat sensing device might include a plurality of sensors to improve detection of sweat analytes, including a volumetric sweat rate sensor, a sweat conductivity sensor, a pH sensor, a GSR sensor, a temperature sensor, a skin impedance sensor, a capacitive skin proximity sensor, and an accelerometer. Many of the auxiliary features of the invention may, or may not, require other aspects of a sweat sensing device, including two or more counter electrodes, reference electrodes, or additional supporting technology or features, which are not captured in the description herein, such as an onboard real-time clock, onboard flash memory (i.e., 1 MB minimum), Bluetooth™, Listnr™, or other communications hardware, and a multiplexer to process a plurality of sensor outputs.

The disclosed sweat sensing device also includes computing and data storage capability sufficient to operate the device, which incorporates the ability to conduct communication among system components, to perform data aggregation, and to execute algorithms capable of generating notification messages. The device may have varying degrees of onboard computing capability (i.e., processing and data storage capacity). For example, all computing resources could be located onboard the device, or some computing resources could be located on a disposable portion of the device and additional processing capability located on a reusable portion of the device. Alternatively, the device may rely on portable, fixed or cloud-based computing resources.

The sweat sensing device's data aggregation capability may include collecting all of the sweat sensor data generated by the sweat sensing device or communicated to the device. The aggregated sweat sensor data could be de-identified from individual wearers, or could remain associated with an individual wearer. Such data can also be correlated with outside information, such as the time, date, medications, drug sensitivity, medical condition, activity performed by the individual, motion level, fitness level, mental and physical performance during the data collection, body orientation, the proximity to significant health events or stressors, age, sex, health history, or other relevant information.

The reader device or companion transceiver can also be configured to correlate speed, location, environmental temperature or other relevant data with the sweat sensor data. The data collected could be made accessible via secure website portal to allow sweat system users to perform safety, compliance and/or care monitoring of target individuals. The sweat sensor data monitored by the user includes real-time data, trend data, or may also include aggregated sweat sensor data drawn from the system database and correlated to a particular user, a user profile (such as age, sex, or fitness level), weather condition, activity, combined analyte profile, or other relevant metric. Trend data, such as a target individual's hydration level over time, could be used to predict future performance, or the likelihood of an impending physiological event.

Such predictive capability can be enhanced by using correlated aggregated data, which would allow the user to compare an individual's historical analyte and external data profiles to a real-time situation as it progresses, or even to compare thousands of similar analyte and external data profiles from other individuals to the real-time situation. Sweat sensor data may also be used to identify wearers that are in need of additional monitoring or instruction, such as the need to drink additional water, or to adhere to a drug regimen.

Because the sweat sensing device could produce potentially sensitive physiological data, some database fields will be routinely encrypted. A preferred encryption method is the Advanced Encryption Standard. The device will access a random 128-bit encryption and decryption key that will be generated and stored by a companion reader device when needed for data transmission. In addition, because some sweat sensor data may repeat frequently, additional protection will be provided by introducing a random initialization vector before the encryption of each value. This will prevent observable patterns from emerging in the encrypted sweat sensor data. Other encryption methods and steps may be required and will be applied according to best practices, as known to those skilled in the art.

Figure 2:
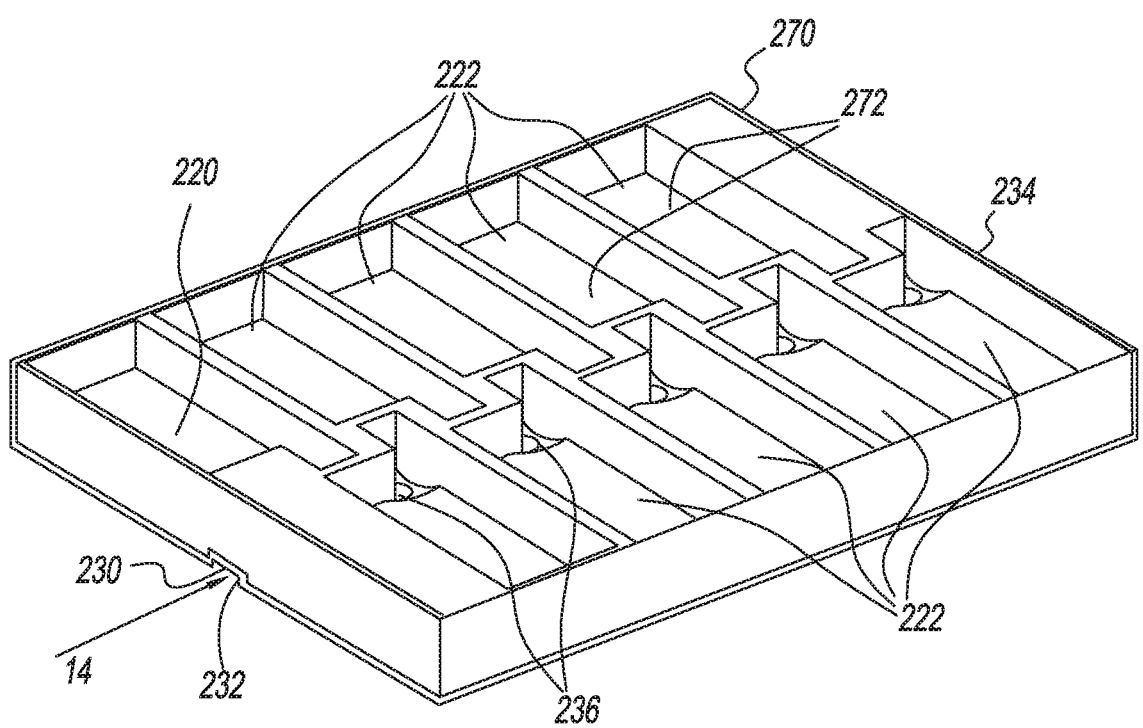
FIG. 2 is an example embodiment of the disclosed invention including a cassette design for ion selective electrodes and a reference electrode for use in a wearable sweat sensing device.

With reference to FIG. 2, an embodiment of the disclosed invention is depicted that includes a suspension-based reference electrode and at least one suspension-based ion-selective electrode. The depicted embodiment includes a cassette housing 270, which has a plurality of wells 272 arranged along a microfluidic channel 230 for transporting sweat through the device. The channel includes an inlet 232, an outlet 234, and a plurality of ion exchange ports 236, one for each of the wells. The suspension in the reference and ion-selective electrodes serves as a structure for suspending salts that allow the exchange of ions between the electrode and the sweat sample. In some embodiments, the suspension material will be one or more hydrogels, e.g., polyvinylpyrrolidone (PVP), collagen, gelatin, or poly alkylene glycol (PAG). The hydrogel suspension material is an aqueous polymer matrix that substantially resists flow when in its steady state. This property allows the salt bridge salt and the reference salt to remain in their respective suspension layers, while allowing the free exchange of ions between the electrode and the sweat sample. In other embodiments, the suspension material is one or more thixotropic compounds, e.g., fumed silica, which mechanically stabilize the salt solutions within the compound, thereby facilitating free ion exchange with the sweat sample. Thixotropic compounds are desirable for certain applications because, relative to hydrogels, they are more resistant to bubble formation, do not require water-tight sealing, and prevent the electrode fluid from leaking out the ion exchange ports. Additionally, use of a thixotropic compound supports more typical manufacturing practices, since it does not require thermally- or chemically-initiated crosslinking of the polymer matrix, i.e., the thixotropic suspension can be directly injected into the sensor well. Some embodiments employ at least one hydrogel and at least one thixotropic compound as suspension materials. In another embodiment (not shown), only the reference electrode is suspension-based, and the ISEs are comprised of ionophore polymers that are screen-printed on electrodes placed on a PVC or PET substrate, as disclosed in PCT/US15/55756, filed Oct. 15, 2015, and PCT/US17/56750, filed Oct. 16, 2017, each of which is hereby incorporated by reference herein in its entirety.

Figure 3:
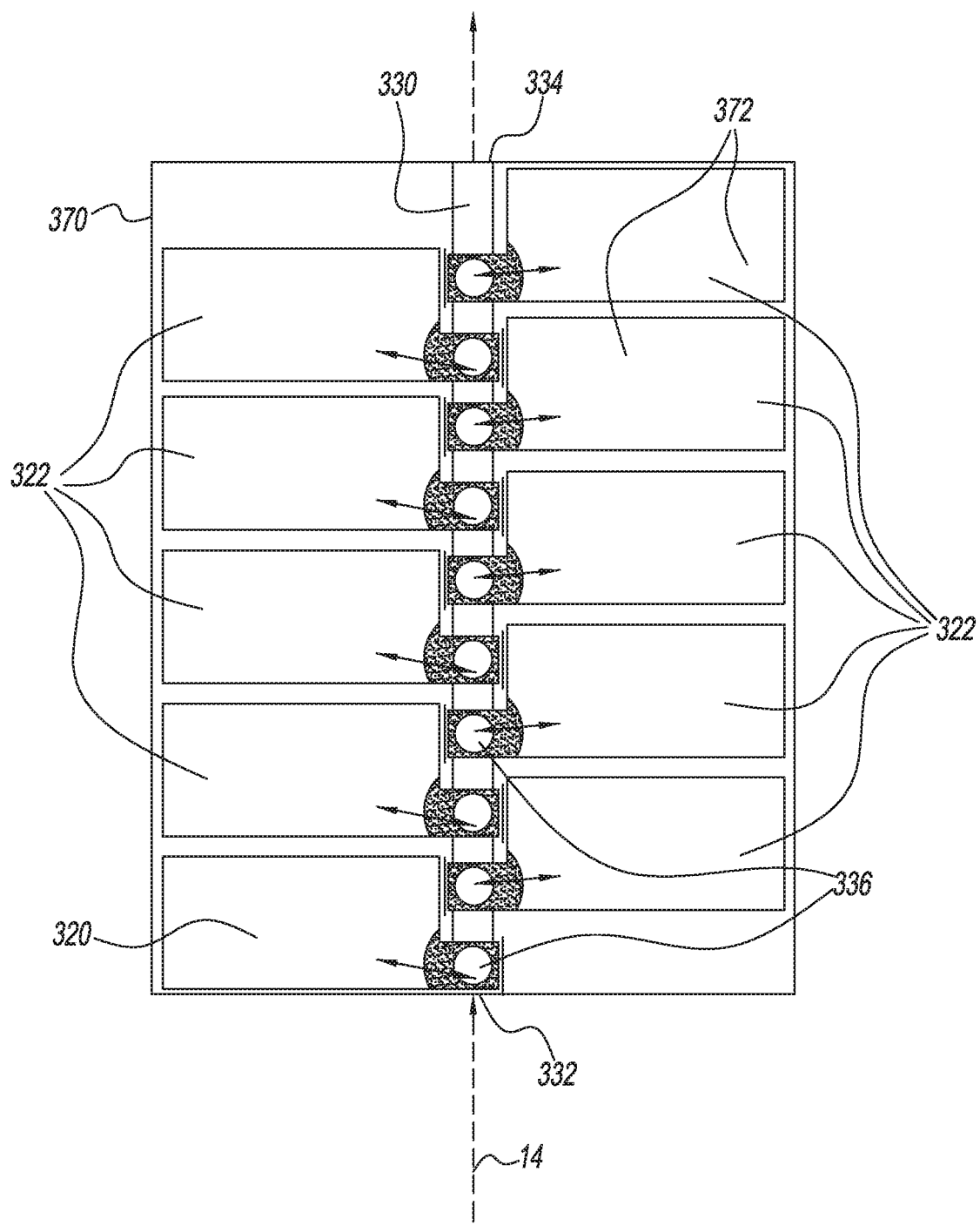
FIG. 3 is a top view of a cassette design for ion selective electrodes and a reference electrode for use in a wearable sweat sensing device.

FIG. 3 depicts a top view of the cassette of FIG. 2, with like numbers referencing like elements of previous figures (e.g., 220 and 320 both represent reference electrodes). At least one well 372 contains an ion selective electrode 322 (nine are shown) and one well contains a reference electrode 320. The reference electrode is preferably located at the front of the channel nearest the inlet 332 to allow operation as soon as possible after sweat enters the channel. In operation, sweat 14 flows through the inlet 332 and into the microfluidic channel 330, where the sweat interacts with the reference electrode 320 and ISE(s) 322 via the ion exchange ports 336. As sweat interacts with each ISE 322, target ions will be selectively exchanged through the ports 336 as the sensor detects the difference in electrical potential between the sweat sample and the ISE for the ISE's target ion. The device then translates the detected voltage into a concentration value for the target ion according to the Nernst equation.

The reference electrode 320 behaves similarly, but is configured to exchange ions non-selectively through its port 336 so that the electrode maintains a consistent and stable voltage for comparison to the ISEs. Over time, the ISEs 322 and reference electrode 320 will leak ions out of the ports 336, eventually becoming depleted of the requisite ions and ceasing to function. The time required for such ion depletion is the operational lifespan of the ISE/reference electrode. This lifetime can be extended by, e.g., reducing the surface area of port 336, which reduces the rate at which ions leave the wells; or by increasing the well volume.

The housing 370 is constructed of a rigid, water-impermeable thermoplastic such as acrylonitrile butadiene styrene ("ABS"). While ten wells 372 are depicted, the cassette may only include one well containing a reference electrode. In other embodiments, the cassette includes only two wells, e.g., an ISE well for detecting $Na^+$ and a reference electrode well, or in still other embodiments, includes a plurality of wells to detect additional analytes, improve accuracy, or to provide redundancy. The wells are depicted as cuboid in shape, but may take other shapes, such as wells having rounded outer edges, as required by space requirements on the device, ergonomics, and other similar considerations. The well volume is subject to several variables, including application requirements, or the individual ISE/electrode requirements, such as operational lifespan. For example, because the ISEs/electrode will become ion-depleted during operation, well volume must account for the durational requirements of the application. For most applications, a well volume of at least 20 μL should be sufficient for 24 hours of operation. Additionally, the ion exchange characteristics of each sensor/electrode must also be considered. The reference electrode will become ion depleted much more rapidly than the ISEs, so the reference electrode well volume could be larger than the ISE wells, e.g., 2× or 3×. Therefore, well volume can be optimized for each ISE or reference electrode, which will translate to a range of configurations, shapes and footprints for the wells 372 and cassette housing 370.

Figure 4:
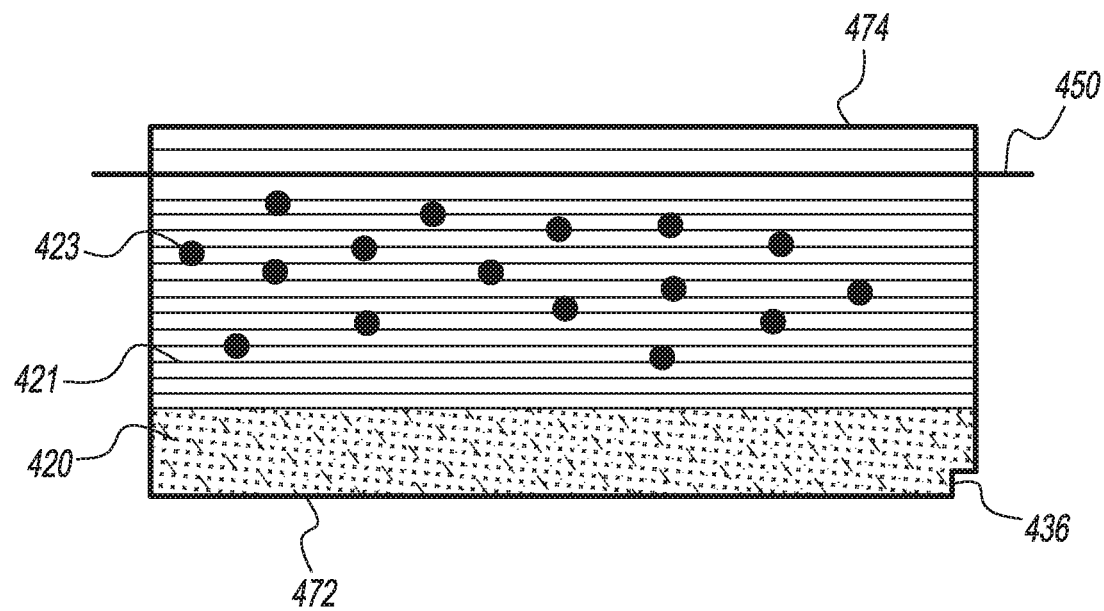
FIG. 4 is an example embodiment of the disclosed invention including a suspension material in an ion selective electrode for use in a wearable sweat sensing device.

With reference to FIG. 4, where like numbers refer to like elements of previous figures, a suspension-based ISE sensor of the disclosed invention is depicted. The ISE is situated within a sensor well 472 of the cassette, which includes an ion exchange port 436. The sensor includes a first layer comprising an ion selective material 420, that is deposited at the base of the sensor well 472, and is in fluid communication with the port 436. In fluid communication with the ion selective material is a hydrogel, a thixotropic compound, or other suspension material layer 421, which is infused with a salt 423 which contains the target analyte, e.g., NaCl for detecting $Na^+$. The molarity of the salt within the suspension material layer will be proportional to the molarity of the target ion in sweat to facilitate accurate sensing. ISEs for low concentration ions, such as $Mg^{2+}$ or $Zn^{2+}$ will contain suspension materials with lower internal analyte concentrations relative to the ISEs for more abundant ions. For example, if $Na^+$ is normally present in sweat at 100 mM, then the suspension material would contain ≈100 mM of NaCl. Similarly, if $Mg^{2+}$ is present in sweat at 100 μM, then the suspension material would contain ≈100 μM of $MgCl_2$. The sensor also includes an electrode 450, which is, e.g., a stabilized Ag/AgCl wire, and which is in fluid communication with the suspension material layer 421. The electrode 450 is preferably embedded in the suspension material, and immobilized to minimize movement while the device is being worn. The sensor well 472 is covered with a protective non-vapor transmissible layer 474, made from, e.g., PET. The ISE sensor can be configured to detect one or more of the following target analytes: $H^+$; $Na^+$; $Cl^-$; $K^+$; $NH_4^+$; $Mg^{2+}$; $Zn^{2+}$; $HPO_4^{2-}$; and $HCO_3^-$; and ammonium ($NH_4^+$).

Figure 5:
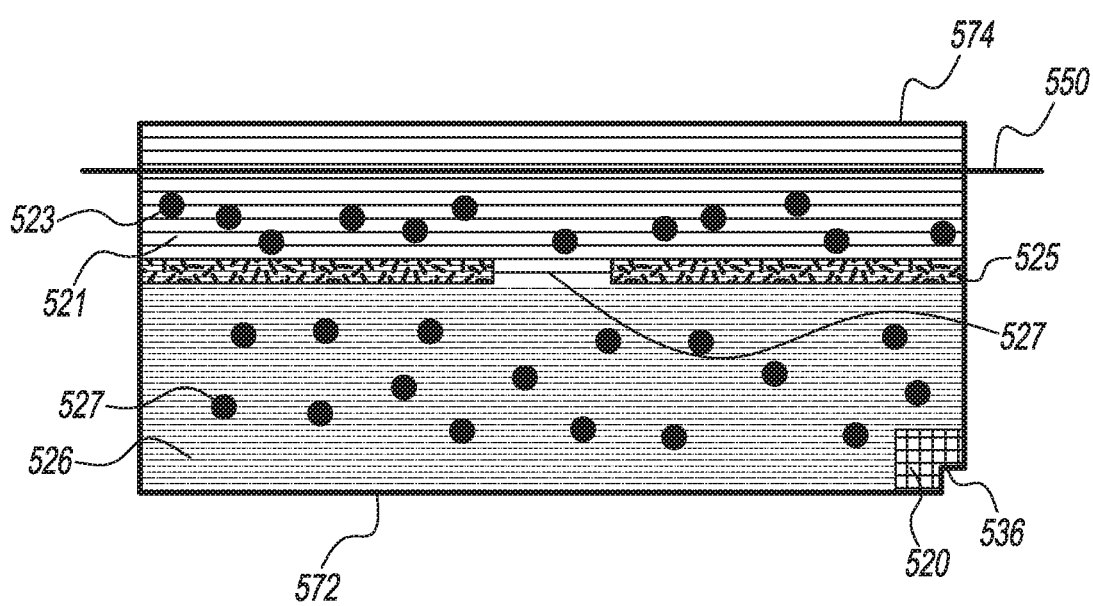
FIG. 5 is an example embodiment of the disclosed invention including a suspension material in a reference electrode for use in a wearable sweat sensing device.

With reference to FIG. 5, where like numbers refer to like elements of previous figures, a suspension material-based reference electrode of the disclosed invention is depicted. The reference electrode is situated within a sensor well 572 of the cassette, which includes an ion exchange port 536. The sensor includes a membrane 520, that is positioned between the port 536 and the remainder of the well contents. The membrane may be, e.g., a track-etched membrane, a dialysis membrane, an osmotic membrane, or any membrane that allows the exchange of ions, but otherwise minimizes interaction between the sweat sample and the contents of the reference electrode well. A semi-permeable dialysis membrane would allow free exchange of ions between the well contents and the sweat sample. The membrane's molecular mass cut-off limit could be customized to provide the ion diffusion speed required for adequate reference electrode performance. The membrane could have pores ranging in size from 10's of nms to 100's of μms. Similarly, a track-etch membrane could have appropriately-tuned nanopore sizes to facilitate free ion exchange. Another approach would be to use multiphase membranes having hydrophobic regions and hydrophilic regions that are configured to facilitate free ion exchange through variation in region size and composition.

In addition to such chemically simple membranes, certain chemically complex membranes, e.g., a zwitterionic polymer membrane, may also be used. The zwitterionic rien-.brane could be constructed by taking a standard polymer backbone and adding two ionic moieties, one a cation and the other an anion. The type, number, and ratio of moieties per unit chain could be varied to optimize ion exchange for the reference electrode for each application. Various amino acids are available as general moieties, while anion moieties include sulfates, phosphates, siliconates, borates, nitric acids, and carboxylic acids; and cationic moieties include substituted aromatic amines, amines, transition metals, and metalloids. Alternately, a suitable zwitterionic membrane could be purchased off the shelf. Ion exchange resin membranes, in which charged ion groups are attached to a polymer matrix, can also be used. Such materials are capable of modification to promote the rapid and selective ion exchange required by the reference electrode. Some ISE embodiments may include a protective suspension layer (not shown) in place of the membrane 520. In other embodiments, suspension-based ISEs also include such tunable membranes (not shown), as described for the disclosed reference electrode, to provide the performance characteristics required by an application.

In fluid communication with the membrane 520 is a salt bridge hydrogel, thixotropic compound, or other suspension material layer 526, which is infused with a hygroscopic and stable salt 527 that tends to not contaminate the sweat sample, e.g., $MgSO_4$. In fluid communication with the salt bridge layer 526, is a reference suspension material layer 521, which is infused with a reference salt 523. The reference salt must be a salt that is highly soluble in water and that contains the reference analyte, e.g., KCl for the reference analyte $Cl^-$. Some embodiments include a contact restriction barrier 525 that includes at least one opening 527, and that reduces the contact area between the salt bridge suspension material and the reference suspension material. Such a partial barrier acts to extend the lifetime of the reference electrode by slowing ion diffusion between the two suspension materials, and is a material similar to the membrane, or is an extension of the ABS housing. The sensor also includes an electrode 550, which is in fluid communication with the reference suspension material layer 521. The electrode 550 is preferably embedded in the reference suspension material, and stabilized or immobilized to minimize movement while the device is being worn. The sensor well 572 is covered with a non-vapor transmissible protective layer 574, comprised of, e.g., PET.

In some embodiments, the salt bridge suspension and the reference suspensions are comprised of at least one hydrogel. In other embodiments, the suspensions are comprised of at least one thixotropic compound, such as fumed silica. In other embodiments, at least one suspension material is a hydrogel and at least one suspension material is a thixotropic compound.

Figure 6:
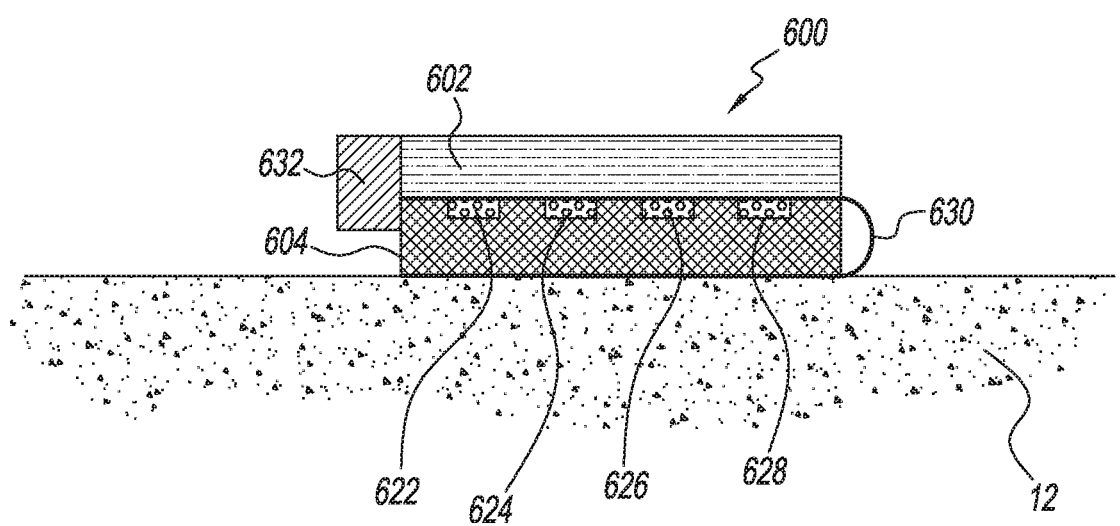
FIG. 6 depicts at least a portion of an embodiment of the disclosed invention.

With reference to FIG. 6, a sweat sensing device for determining electrolyte loss as disclosed herein is placed on skin 12. The device 600 includes a reusable component 602 and a disposable component 604. The disposable component may contain a wicking collector 630 or microfluidic channel (not shown) which will be in fluidic communication with the skin 12 while the device is in use. The wicking collector transports sweat from the skin to a plurality of analyte-specific sensors 622, 624, 626, 628 arranged in an array. Said analyte-specific sensors may include, for example, ion-selective sensors for $Na^+$, $Cl^-$, $K^+$, and $H^+$. Sensors can be screen printed or suspension material ISEs, as disclosed in U.S. Provisional Application No. 62/526,810, filed Jun. 29, 2017. In other embodiments, the device may use a combination of screen printed and suspension material ISEs, e.g., the reference electrode could be a suspension material configuration, while the ion selective sensors are ionophore polymers that are screen printed on electrodes.

Some embodiments may include a wicking pump 632 in fluidic communication with the collector 630 to facilitate sweat flow across the sensors. Other embodiments may include a plurality of secondary sensors, including volumetric sweat rate, micro-thermal flow rate, GSR, sweat conductivity, impedance or capacitance sensors for skin contact measurement, or a temperature sensor (not shown). In other embodiments, the device may include additional analyte-specific sensors, such as electrochemical aptamer-based sensors or amperometric sensors, that are capable of measuring biomarker concentrations, e.g., biomarkers indicative of dehydration or stress. The disposable component 602 will be fluidically connected to the reusable component 604, and in some embodiments will be electrically connected to the reusable component. The device will be secured to the wearer's skin by various means, including a removable adhesive layer, an elastic band or strap, a clothing element, such as a compression sleeve, etc. (not shown), so long as fluidic contact is maintained between the device and skin sufficient to allow device operation.

Figure 7:
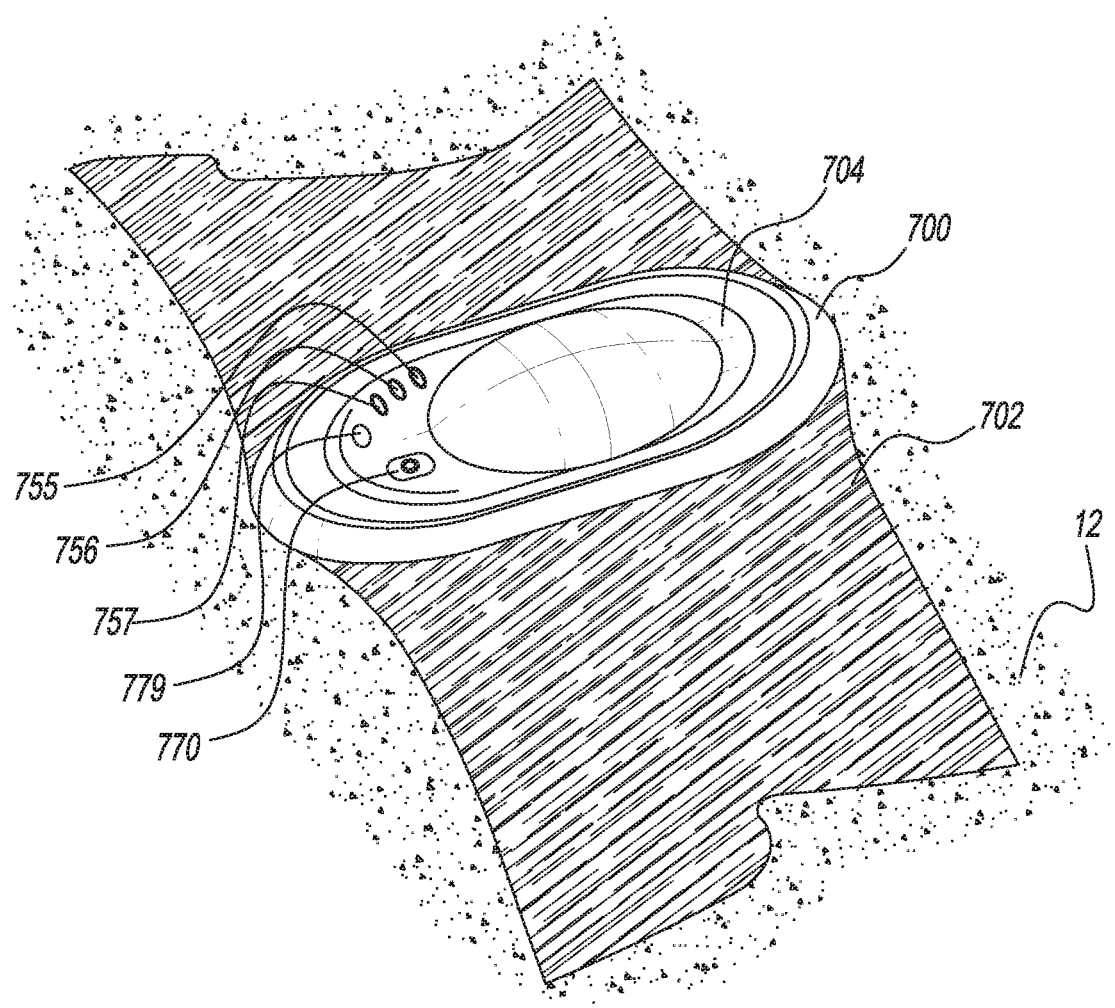
FIG. 7 depicts at least a portion of an embodiment of the disclosed invention having reusable components and disposable components.

With reference to FIG. 7, an exterior view of a sweat sensing device 700 of the disclosed invention is depicted secured to a wearer's skin 12 by a flexible strap 702. The reusable component 704 will be configured to communicate outputs with the wearer by various means. For example, the device may include one or more lighted indicators 755, 756, 757, which can be the same color or a plurality of different colors, e.g., one red, one yellow, and one green light. Alternately, LED lights may be configured as a readable display, or the device may include a liquid crystal display (not shown). In some embodiments, the device may include auditory alerts and signals that communicate device outputs. In other embodiments, the device may include haptic output signals. The different output means may also be used in combination to facilitate communication with the wearer in various applications or contexts.

The device will also be configured to receive inputs from a device user or wearer. In addition to input communications from a reader device, the device may also include components that allow direct inputs from a device user. For example, the device may include at least one button 779 which relays inputs from the user. In another example embodiment, the light indicators 755, 756, 757 may be co-located with input buttons to allow inputs from the user. In other embodiments, the device may include a touch screen, an optical input component 770, such as a camera or laser scanner, that is configured to read a bar code, QR code, or other visual input. Some embodiments may include near field communications capability, such as an RFID communications system, Bluetooth™, Blue Robin™, Listnr™, and other embodiments may communicate via cellular or wireless internet. These inputs can be used to inform the device about the wearer's electrolyte status prior to, at the beginning of, or during device use. Inputs may also improve device function during use by providing information about electrolyte and fluid intake, electrolyte or fluid loss through non-sweat means (such as urinary excretion), or other relevant information.

For an example use scenario, the electrolyte loss monitor 700 would be secured to an endurance runner's bicep by the flexible strap 702. The wearer would use a smartphone to initialize the device, which could include entering or downloading from a database information about the wearer's recent fluid and food intake, fluid loss, recent training, weather conditions, or other relevant inputs. Once the device is initialized, the wearer would begin running and would begin to sweat. The device would measure electrolyte concentrations in the wearer's sweat at chronologically assured sampling intervals. The device would process the sweat electrolyte data, producing, for example, sweat electrolyte concentration, concentration trend information, or ratios of concentrations among the various monitored electrolytes. Using an algorithm, the device would then determine an electrolyte loss estimate as compared to a baseline value for the wearer reflecting an expected or normal concentration, trend, or ratio, where said baseline reflects relevant characteristics of a wearer profile, which may include information such as the individual's skin temperature, sweat rate, heart rate, age, sex, initial hydration state, body mass index, transdermal evaporative fluid loss, kidney health, fitness level, heat acclimation level, fluid adsorption rate capacity, and recent physical activity, or comparisons to another person or persons with similar relevant characteristics; or external factors, such as altitude, air temperature, and humidity. Depending on the electrolyte loss estimate, the device would then communicate the results to the wearer, for example by auditory alert, a haptic signal, a light signal, or a combination of these.

The device outputs and physical input components as described may be used by the wearer in real time to inform the wearer's electrolyte status. For example, the device could display a green light indicating only water is required to be consumed at that time. The wearer would press the green indicator button, turning off the alert, and causing the device to run an algorithm to record fluid intake of a standard amount, such as 8 fluid ounces. In another example, the device may display a red light indicating an urgent need for a coded or recommended amount of electrolyte replenishment. The wearer would then place a package of the coded or recommended electrolyte dose, such as a commercial electrolyte replenishment gel, drink, or chew, over the optical scanner. The scanner would read the package's bar code, causing the device to turn off the light indicator, and to run an algorithm to record the electrolyte intake. Some embodiments may include an RFID communications system, which is able to interact with an RFID tag placed on the electrolyte packaging. In another scenario, the wearer may press an input button 779 that informs the device that a fluid loss event, such as urination or vomiting, has occurred during device use. The device can then update its electrolyte status model to account for the lost fluids and electrolytes, as input by the wearer.

Figure 8A:
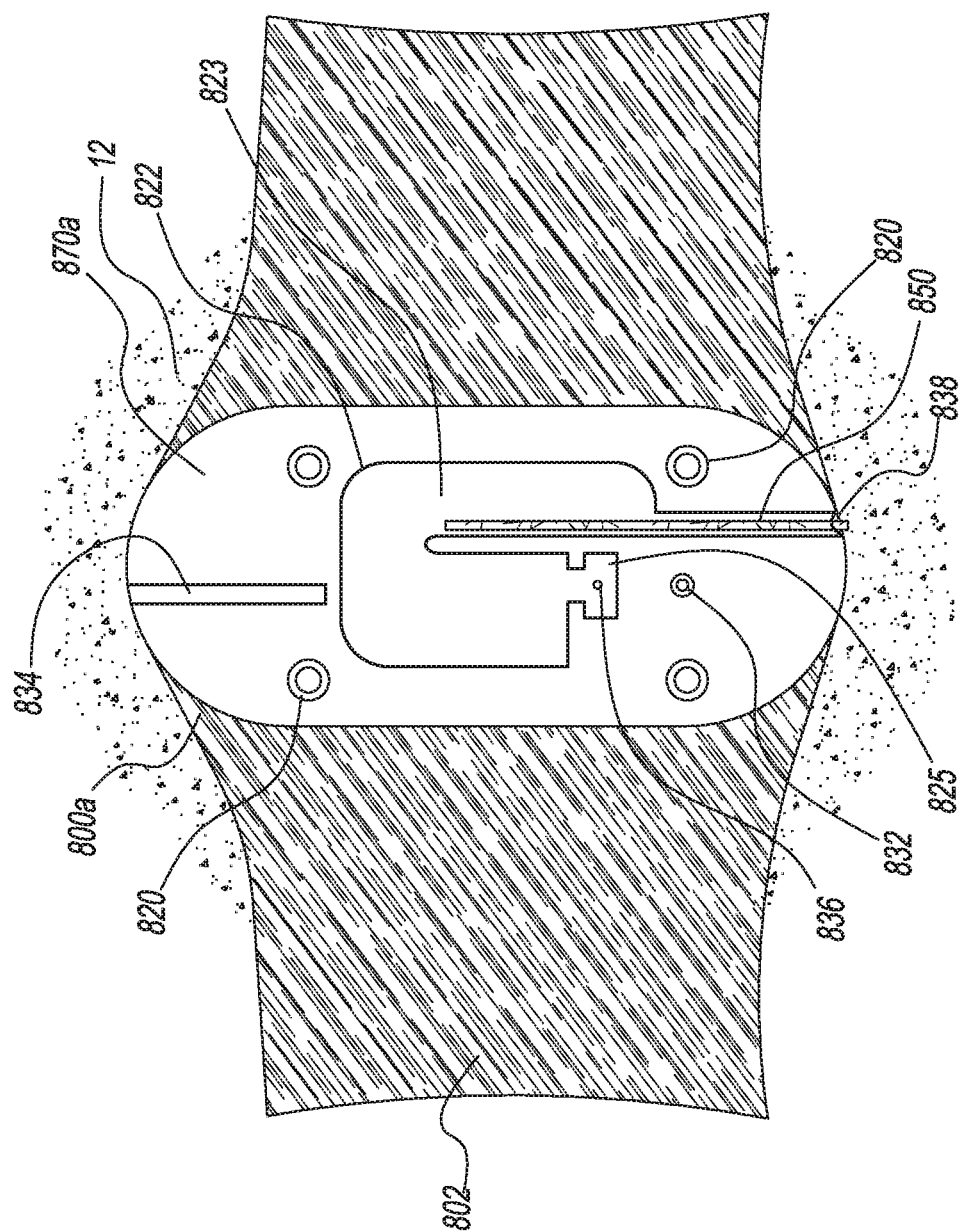
FIG. 8A depicts a cross section of an embodiment of the disclosed invention.

Some embodiments of the disclosed device may include a galvanic skin response (GSR) sensor, a sweat conductivity sensor and a volumetric sweat rate sensor, all of which can be used in conjunction with contemporaneous ISE-derived sweat ion measurements to provide improved sweat ion concentration and sweat rate data. For example, with reference to FIG. 8A, a top view of a first layer 800a of a device of the disclosed invention is depicted. The sweat sensing device is configured to be worn on skin 12 and secured by a flexible strap, band, or sleeve 802 made from neoprene, spandex, elastic or other suitable material capable of holding the device against skin comfortably while preventing excessive movement of the device relative to the skin. The depicted layer of the device comprises a water impermeable substrate 870a, which carries a plurality of electrodes 820 (four are shown) for sensing galvanic skin response ("GSR"). One or more of these electrodes 820 can also be configured to include a temperature sensor (not shown). These sensors pass through the substrate and contact the wearer's skin 12 when the device is worn. This layer also includes a reference electrode 822, comprised of a reference chamber 823 for containing a fumed silica matrix mixed with a reference electrolyte compound, e.g., KCl, a fill port 838 for replenishing the reference electrolyte, a salt bridge chamber 825 containing a fumed silica matrix mixed with a salt bridge compound, e.g., $MgSO_4$, a port 836 to allow the reference electrode to be in fluid communication with ISE sensors that are configured on a second layer (depicted in FIG. 8B), and a wire electrode 850, made from, e.g., Ag/AgCl. In some embodiments, the port 836 includes a selectively permeable membrane, as described above for membrane 520 of FIG. 5. The reference chamber 823 is shaped to improve ion exchange with wire electrode 850. As depicted, this port 836 will is located upstream of the ISEs on the second layer, meaning that as new sweat emerges from the body and enters the device, the sweat will interact with the reference port 836 prior to reaching the ISEs. In other embodiments however, the port will be located downstream of the ISEs. The first layer also includes an inlet 832 for transporting sweat collected from the skin 12 to the microfluidic channel that is also configured on the second layer.

Figure 8B:
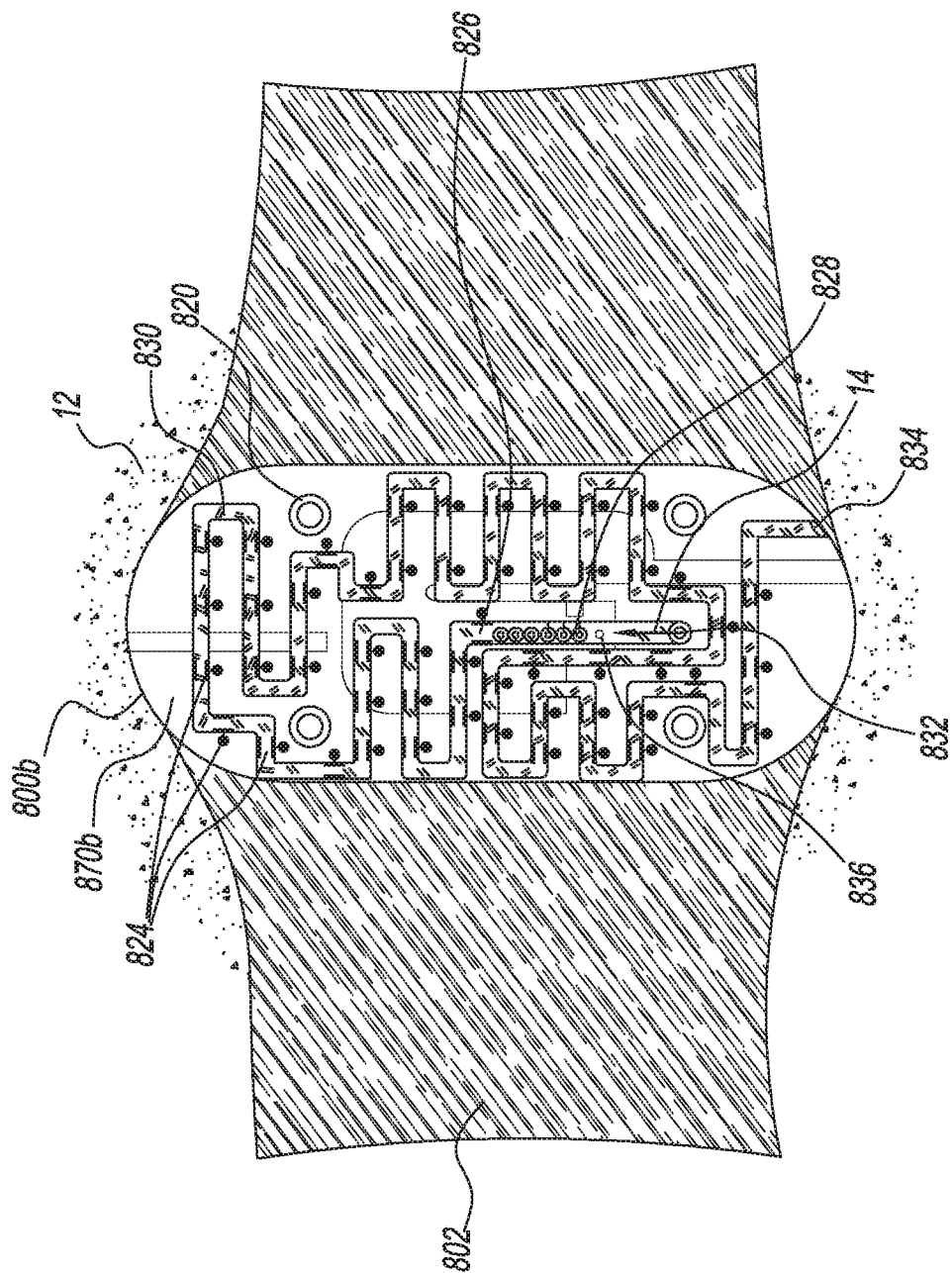
FIG. 8B depicts a cross section of an embodiment of the disclosed invention.

Said second layer 800b of the device is depicted in FIG. 8B. As with the first layer, this layer also comprises a water impermeable substrate 870b. The first layer and second layer are not necessarily arranged in the depicted order relative to the wearer's skin, i.e., in some embodiments, the second layer can be located closer to the skin than the first layer. The substrate houses a microfluidic channel 830 that is configured to receive sweat from the skin and convey the sweat sample to a plurality of sensors. Some embodiments may use a microfluidic textile or wick rather than the channel as shown. The sensors include a plurality of ion selective electrodes 828 (six are shown), one or more sweat conductivity sensors 826, and a plurality of volumetric sweat rate sensor electrodes or switches 824. The channel 830 is cut into the substrate, or the entire part will be injection molded and sensor electrodes added afterward. The channel has a volume, e.g., several nL. Some embodiments will include air traps or air bubble venting components to prevent air bubbles from interfering with measurements taken by electrodes or other sensors. During operation, sweat enters the channel 830 via the inlet 832, and moves through the channel in the direction of the arrow 14. Once sweat reaches the port 836, it enters fluidic communication with the reference electrode, and then progresses to contact the sweat conductivity sensor 826, where the total electrolyte content of the sweat sample will be measured. As sweat continues to fill the channel 830, the sweat sample will move across the ISEs 828, which work in conjunction with the reference to measure sweat concentrations of electrolytes, such as $Na^+$, $Cl^-$, $K^+$, $Mg^+$, etc. Then sweat will contact the volumetric sweat rate switches 824 that are arranged along the channel at known intervals from each other, so that the channel volumes between switches are determined, e.g., 1-5 nL. The rate at which additional switches are closed by the sweat sample, coupled with the volume of the channel section that is filled with sweat, provides a sweat rate value. Because of space limitations on the wearable device, volumetric sweat rate channels have limited operational lifespans that may not cover an entire application period. For example, at moderately high sweat rates, i.e., 10 nL/min/gland, a device as disclosed having a sweat collection area of about 2 $cm^2$ would operate for about 2 hours. The channel design can be modified to facilitate individual applications by varying channel geometry (length, cross section, path geometry), inner surface treatments, or switch spacing. Some embodiments include a sweat collecting pump or reservoir (not shown), or include a drain 434 to pass sweat out of the device.

The substrate is configured to allow the GSR electrodes 820 to pass through the second layer and, when the device is assembled, contact the printed circuit board layer (not shown), so that the electrodes facilitate electrical communication between the skin 12 and device electronics. The device also may include additional layers (not shown), including a printed circuit board layer for carrying electronics, communication, and processing capability, a battery, a water impermeable cover, among other components.

By combining contemporaneous ISE electrolyte measurements, GSR, sweat conductivity, volumetric sweat rate, and skin temperature on a single device, the disclosed invention provides a number of advantages over existing capabilities. Chief among these advantages is the ability to foster redundancy and feedback loops among device sensors to improve the quality of information derived from a device wearer's sweat. As disclosed in U.S. application Ser. No. 15/653,494, incorporated herein by reference in its entirety, contemporaneous GSR, sweat conductivity and volumetric sweat rate measurements provide redundancy to sweat rate calculations. The disclosed invention can provide an additional layer of redundancy through use of ISEs. Because sweat concentrations of $Na^+$ and $Cl^-$ are highly dependent on sweat rate, ISE-derived concentrations for these electrolytes can be correlated to a sweat rate through a look-up table, a database, or other means. Together, these four sensor modalities can provide a composite sweat rate estimate, for example, by calculating a weighted average of the four estimates, or by using the estimates to create a profile. Comparisons between volumetric sweat rate, GSR-derived sweat rate, conductivity-derived sweat rate, and ISE-derived sweat rate can therefore be built to provide a calibrated profile for an individual over multiple uses, or for a device over a single use.

In addition to redundancy, such comparisons of ISE-derived sweat rate to GSR/conductivity/volumetric sweat rate can be used to mitigate shortcomings in ISE measurements, and vice versa. For example, a characteristic of the disclosed design is that GSR and sweat conductivity sensors will measure new sweat at an earlier time than the ISEs, resulting in the need to synchronize measurements among the different sensor modalities, so that measurements of the same sweat sample are compared. The device may also account for the relative position of the ISEs, since those ISEs closer to the inlet 832 will see new sweat earlier than the downstream ISEs. In addition, sweat will tend to pool over the ISEs, especially during periods of decreased or no sweating. While it pools over the ISEs, old and new sweat will tend to mix in the chamber 830 in the vicinity of the ISEs, so changes in ISE concentration registered by the device during such periods will primarily be due to mixing of old and new sweat. As a result, while the ISEs are measuring more or less continuously, the chronologically assured data will be much more limited, and will be related to sweat rate, the surface area of the ISE electrode, and the channel volume. Because GSR can be the most responsive modality to sweat initiation, rate change, and cessation, GSR readings will be used to indicate the time sweating initiates, decreases, or stops altogether. Similarly, the timing of changes in the measurements by other sensors, such as sweat rate, sweat conductivity, or skin temperature, can also be used to improve ISE measurement quality. ISE measurements during periods of decreasing or ceased sweat rate can then be corrected, weighted less, or discarded to account for sensor response lag, and more responsive sensor modalities, i.e., GSR, can be weighted more or used exclusively to inform sweat rate and ion concentration.

Another aspect of ISE measurement of sweat ion concentrations is the need to take measurements at chronologically assured intervals. Sweat rate measurements from the other sensor modalities, combined with the known volume of the channel 830 can be used to assess whether the sweat sample contacted by an ISE is new sweat, old sweat (i.e., sweat that has already been measured) or a mixture of old and new sweat. For example, volumetric sweat rate measurements, combined with the channel volume near the ISE could be used to set a chronologically assured sampling interval, so that the ISE only measures ion concentration when the sweat sample is predominately, or all, new sweat. Alternately, the device could use sweat rate and channel volume to determine a sweat sample's relative mix of old and new sweat, and by comparison with previous readings, determine the ion concentration of the new component of such a mixed sweat sample. Another solution is to intersperse reference ISEs, e.g., $Cl^-$ ISEs, among the ISE sensor suite to measure the amount of mixing that is taking place. During periods of decreased sweat rate, concentration changes along the channel will likely be from sample mixing, and should be detected by the reference ISEs.

Similarly, since GSR readings are comprised of three components (sweat rate, sweat ion content (conductivity), and skin contact resistance), ISE measurements of ion content can be used to inform GSR measurements. For example, ISE ion measurements could be mapped to a GSR change to determine the relative contribution of sweat rate change or skin contact resistance change. ISE measurements could also calibrate GSR measurements to correct for large person-to-person and use-to-use variabilities in the GSR skin contact resistance component. For example, when a sweat sensing device is first activated and taking measurements on a wearer, the device may compare ISE ion concentration, sweat conductivity, and GSR changes throughout the three GSR sweating regimes. The device could then correlate $Na^+/Cl^-$ concentrations to GSR/sweat conductivity readings for each regime, and by extension, a calculated sweat rate. Then, during subsequent sweating cycles, the device could measure $Na^+/Cl^-$ concentration changes, sweat conductivity change, and GSR change to calculate a sweat rate based on the calibrated relationship among the sensor modalities in the appropriate sweat regime. This composite sweat rate may then be compared to the sweat rate developed by the volumetric sensor.

Because of their overlapping and complimentary attributes, the four sensor modalities can be used in concert to provide improved electrolyte loss measurements through the use of continuous feedback loops. For example, the interpretation of instantaneous sweat rate and ion concentration readings from the four modalities can be refined and updated as additional data is acquired. If at time t0, a device wearer begins to sweat, and at t1, the GSR, and sweat conductivity sensors begin measurements. Sweat rate measurement for t1 will necessarily be a rough estimate, based only on the two sensor modalities. At t2, ISEs and volumetric sweat rate sensors take their first reading. From this point, the ISEs, GSR and sweat conductivity measurements can be taken more or less continually, while volumetric sweat rate will be periodic, based on sweat traveling in the channel to the subsequent switch. At t3, sweat reaches the second volumetric switch, and a new sweat rate estimate is determined. Not only can the device compare the different sensor modalities to develop a composite sweat rate, but the device can also reach back to refine previous ISE measurements based on the chronologically assured sampling interval indicated by the sweat rate. The corrected ISE measurements from time t2 can then be used to improve sweat rate and ion concentration measurements taken at t3. During periods of decreasing sweat rate, such refinements will be especially important.

Embodiments of the disclosed invention can also include a means to determine if the sweat sensing device is being worn by an individual, and whether it is in proper skin contact to allow accurate sweat sensing device readings, as disclosed in PCT/US15/55756, which is incorporated herein in its entirety. This may be accomplished through the GSR electrodes or by use of capacitive sensor electrodes, as are commonly used in consumer wearable health monitoring devices and mobile computing devices. If impedance electrode contact with the skin is, or becomes inadequate, this can be detected as an increase in impedance and the device can send an alert signal to the user or another device. Similarly, capacitance sensors may be placed on selected locations on the skin-facing side of the device, and could convey information about the distance between the device and the skin. Inadequate contact can indicate that the device has been removed by the user, or has become detached from the skin for other reasons.

The sweat sensing device's skin contact sensor(s) may also continuously or near-continuously monitor the adequacy of skin contact during device operation. Inadequate skin contact can affect sensor readings in a number of ways, for example, air bubbles can enter the microfluidic channel. If an air bubble contacts an ISE, sweat conductivity sensor, or volumetric sweat rate switch, the sensor can record an inaccurate measurement. Sensors that rely on contact with the skin, such as GSR, temperature, and certain ISE configurations, can also provide inaccurate measurements if skin contact is insufficient. During times of poor or no skin contact, the device may avoid taking measurements, or may, via algorithm, account for the poor or no skin contact when interpreting or weighting the measurements. The device may also communicate to the wearer or user to inform them of the inadequacy or absence of skin contact and to advise corrective action. Alternately, the device may track periods during which the device is out of contact with skin and discard any collected data, or extrapolate previous measurements to bridge gaps in device use.

This has been a description of the disclosed invention along with a preferred method of practicing the disclosed invention, however the invention itself should only be defined by the appended claims.

What is claimed is:

1. A sweat sensing device configured to be worn on a skin surface of an individual, comprising:
   a first layer, comprising one or more ion selective electrode (ISE) sensors for measuring a concentration of an ion in a sweat sample, the one or more ISE sensors located in a sensor channel, the sensor channel comprising an inlet and an outlet, wherein the inlet is in fluidic communication with the skin surface, and the one or more ISE sensors are located between the inlet and the outlet; and
   a second layer, comprising a water impermeable substrate and a reference electrode, the reference electrode comprising:
   a reference chamber containing a mixture that includes a fumed silica matrix and a reference salt, and including a fill port at a first end of the reference chamber,
   a salt bridge chamber located at a second end of the reference chamber, the salt bridge chamber containing a mixture that includes a fumed silica matrix and a bridge salt, and including an exchange port configured to fluidically connect the reference electrode to the one or more ISE sensors, wherein the exchange port connects to the sensor channel at a location between the inlet and the one or more ISE sensors, and
   a wire electrode extending into the reference chamber from the fill port.

2. The device of claim 1, wherein the one or more ISEs are comprised of ionophore polymers that are screen-printed on electrodes and placed on a substrate.

3. The device of claim 1, wherein the one or more ISE sensors includes an electrode, a suspension material containing a target analyte salt, an ion-selective material, an ion-exchange port, and an ion-exchange membrane; and wherein the electrode is in fluidic communication with the suspension material, the suspension material is in fluidic communication with the ion-selective material, the ion-selective material is in fluidic communication with the ion-exchange membrane, and the ion-exchange membrane is in fluidic communication with the ion-exchange port.

4. The device of claim 3, wherein the suspension material is one of the following: a hydrogel; and a thixotropic compound.

5. The device of claim 1, where wherein the one or more ion selective electrode sensors are capable of measuring a concentration of one or more of the following: $Na_+$; $Cl_-$; $H_+$; $K_+$; $NH_{4+}$; $Ca^+$; $HCO_{3-}$; and $Mg_+$.

6. The device of claim 1, further comprising a secondary sensor chosen from the following: a volumetric sweat rate sensor; a micro-thermal sweat flow rate sensor; a sweat conductivity sensor; and a skin temperature sensor.

7. The device of claim 1, wherein the reference salt is one of the following: KCl.

8. The device of claim 1, wherein the bridge salt is one of the following: $MgSO_4$, and $MgCl_2$.

9. The device of claim 3, wherein the target analyte salt is one of the following: NaCl, KCl, and $MgCl_2$.

10. The device of claim 1, wherein the exchange port further includes a reference membrane comprising one of the following: a dialysis membrane; an osmotic membrane; a track-etch membrane; a multi-phase membrane; a zwitterionic polymer membrane; an ion exchange resin membrane; and a tunable membrane.

11. A method of using the device of claim 1 to monitor an individual's electrolyte levels, the method comprising:
- receiving one or more measurements of a concentration of an ion in a sweat sample with an ion selective electrode (ISE) sensor;
- receiving input relevant to one or more of the following: a hydration status for the individual; an electrolyte status for the individual; a fluid intake for the individual; a fluid output for the individual; an electrolyte intake for the individual; and an electrolyte output for the individual;
- using said measurements and said input to develop one or more of the following electrolyte values: a sweat electrolyte concentration; a sweat electrolyte concentration trend; a sweat rate; and a concentration ratio between a plurality of electrolytes; and
- outputting information derived from the one or more electrolyte values.

12. The method of claim 11, further comprising comparing the electrolyte value to a baseline value, where said baseline value reflects one of the following: a profile for the individual; a profile for one or more persons with similar relevant characteristics to the individual; and external information.

13. The method of claim 12, wherein said baseline value is derived from one of the following: a skin temperature for the individual; a sweat rate for the individual; a heart rate for the individual; an age of the individual; a sex of the individual; an initial hydration state for the individual; a body mass index of the individual; a transdermal evaporative fluid loss for the individual; a kidney health of the individual; a fitness level for the individual; a heat acclimation level for the individual; a recent physical activity level for the individual; relevant characteristics of another person or persons; altitude; air temperature; and humidity.

14. The method of claim 11, further comprising developing the electrolyte value using one of the following: a sweat rate measurement; a sweat conductivity measurement; a sweat onset time; a sweat cessation time; a sweat rate change time; a sweat conductivity change time; and a skin temperature change time.

15. The method of claim 11, wherein said information is one of the following: the electrolyte value; a recommendation to consume an amount of fluid; and a recommendation to consume an amount of electrolyte.

\* \* \* \* \*